United States Patent [19]

Omatsu et al.

[11] Patent Number: 5,196,186
[45] Date of Patent: Mar. 23, 1993

[54] ALKALI METAL ZINC MONOALKYLPHOSPHATE, PARTICLES THEREOF, PROCESS FOR PREPARING THE SAME, AND COSMETIC CONTAINING THE SAME

[75] Inventors: Shinichiro Omatsu; Mitsuharu Masuda, both of Wakayama; Hiroshi Ito, Tokyo; Takashi Imamura, Chiba; Tomihiro Kurosaki, Osaka, all of Japan

[73] Assignee: Kao Corporation, Tokyo, Japan

[21] Appl. No.: 815,225

[22] Filed: Dec. 31, 1991

Related U.S. Application Data

[62] Division of Ser. No. 693,496, Apr. 30, 1991, which is a division of Ser. No. 494,001, Feb. 27, 1990.

[30] Foreign Application Priority Data

Feb. 27, 1989 [JP] Japan ................................. 1-45796
May 25, 1989 [JP] Japan ................................ 1-131989
Sep. 26, 1989 [JP] Japan ................................ 1-249412

[51] Int. Cl.$^5$ .............................................. A61K 7/35
[52] U.S. Cl. ...................................... 424/69; 424/63
[58] Field of Search ................................. 424/63, 69

[56] References Cited

U.S. PATENT DOCUMENTS

4,804,533  2/1989  Fukasawa ............................ 424/63
4,857,308  8/1989  Imamura ............................. 424/69

Primary Examiner—Thurman K. Page
Assistant Examiner—William Benston, Jr.
Attorney, Agent, or Firm—Sughrue, Mion, Zinn, Macpeak & Seas

[57] ABSTRACT

An alkali metal monoalkylphosphate having a saturated or unsaturated straight-chain or branched hydrocarbon group having from 8 to 32 carbon atoms is described; also described is a process for preparing particles of said alkali metal zinc monoalkylphosphate and cosmetics containing said particles.

4 Claims, 2 Drawing Sheets

FIG.1

|←—10μm—→|

FIG.2

|←—10μm—→|

ALKALI METAL ZINC MONOALKYLPHOSPHATE, PARTICLES THEREOF, PROCESS FOR PREPARING THE SAME, AND COSMETIC CONTAINING THE SAME

This is a divisional application of application Ser. No. 07/693,496 filed Apr. 30, 1991, which was a divisional application of application Ser. No. 494,011, filed Feb. 27, 1990.

FIELD OF THE INVENTION

This invention relates to novel alkali metal zinc monoalkylphosphates, particles thereof, a process for preparing the same, and cosmetics containing the same. More particularly, it relates to alkali metal zinc monoalkylphosphates, alkali metal zinc monoalkylphosphate particles mainly composed of platy crystal particles and having excellent performance as a lubricant, a process for preparing the same, and cosmetics containing the same.

BACKGROUND OF THE INVENTION

There are many cosmetics containing powders, such as cosmetics for foundation, cosmetics for make-up (e.g., eye shadow) and cosmetics for the body (e.g., body powder, baby powder). However, it has been found impossible that all of the performances such as smoothness, adhesion, etc., required for cosmetics of good quality are fully satisfied by cosmetic powders conventionally used, for example, inorganic extender pigments such as talc; inorganic coloring materials such as zinc oxide; organic coloring materials such as organic tar dyes; composite pigments such as micaceous titanium; and powders having surfaces treated with conventional coating agents such as silicone.

Accordingly, metallic soaps are often blended with cosmetics to impart smoothness, adhesion, etc., thereto. However, it is not considered that satisfactory performances are fully imparted to such cosmetics by the metallic soaps with respect to smoothness, adhesion, etc.

Spherical polymers such as nylon powder and styrene polymers are also used as cosmetic materials for imparting smoothness, adhesion, etc. However, they have disadvantages in that they are bulky to the feel and adhesion is poor, so that flexibility and wetness can not be imparted to the cosmetics. Further, they have disadvantages in that the adhesion of the cosmetics to the skin is deteriorated and press-moldability is lowered.

The present inventors had previously found that metal salts of monoalkylphosphoric acids have properties such as smoothness, adhesion, etc., suitable for use as cosmetic powders. As a result, a patent application relating to a cosmetic containing the same was filed (see JP-A-1-125314 (the term "JP-A" as used herein means an "unexamined published Japanese patent application")). Further, there was filed a patent application relating to a process for economically preparing metal salts of monoalkylphosphoric acids having performances suitable for use as cosmetic powder by using mixed solvents of water and water-soluble organic solvents as solvents for reaction (see, JP-A-61-229889 (corresponding to U.S. Pat. No. 4,804,533)). The present inventors had already found that among the metal salts of monoalkylphosphoric acids, zinc monoalkylphosphate particles have particularly excellent performance as a lubricant and as a cosmetic powder. However, it was found that after the completion of the formation of zinc salt, the reaction system is strongly acidified (in many cases, PH<2) in the conventional process, and zinc monoalkylphosphates are produced in the crystalline form of needle crystals, or a mixture of platy (including scaly) and needle crystals, or in an amorphous form, under the above acidified conditions. There was much difficulty in preparing zinc monoalkylphosphates mainly composed of platy crystals (including scaly crystal). When such mixtures of variOus crystal forms are used, unevenness in coating is caused, a whitish tone is left behind, and satisfactory performances as a lubricant and as a cosmetic powder can not be obtained. Further, the size of these particles is often non-uniform and it is necessary to provide a classification step and a crushing step when they are used as a lubricant.

Accordingly, it has been highly demanded to develop metal salts of monoalkylphosphoric acids which are excellent in safety and have excellent performances such as smoothness, transparent appearance, adhesion, water repellency, etc. as a lubricant and as a cosmetic powder.

SUMMARY OF THE INVENTION

The present inventors have conducted extensive studies to provide cosmetics which are freed from disadvantages associated with the prior art as mentioned above, have excellent properties such as smoothness, transparent appearance, adhesion, water repellency, etc., and are pleasant to the touch. As a result, it has now been found that there can be prepared alkali metal zinc monoalkylphosphate particles which are predominantly composed of platy crystal particles, scarcely cause agglomeration, contain negligible needle crystals or amorphous particles, have approximately uniform particle diameter, are excellent in safety, and have excellent properties such as smoothness, transparent appearance, adhesion, water repellency, etc., as cosmetic base material by reacting an alkali metal salt of a specific monoalkylphosphoric acid with a zinc salt among materials known as safe ingredients and conventionally applied to cosmetics, and then adjusting the pH of the reaction mixture to a value within a specific range. Further, it has been found that when the resulting particles are blended with cosmetics, there can be obtained cosmetics having such excellent properties that they are well-spread on the skin, adhere well to the skin, do not give a bulky feel on coating, have transparent appearance, and are water-repellent. The present invention has been accomplished on the basis of these findings.

Thus, one object of the present invention to provide alkali metal zinc monoalkylphosphate particles having properties suitable for use as a lubricant and as a cosmetic powder.

Another object of the present invention is to provide a process for preparing said alkali metal zinc monoalkylphosphate particles.

Still another object of the present invention is to provide cosmetics containing said alkali metal zinc monoalkylphosphate particles.

These and other objects of the present invention will become apparent from the following description.

The present invention provides alkali metal zinc monoalkylphosphates having a saturated or unsaturated straight-chain or branched hydrocarbon group having from 8 to 32 carbon atoms, alkali metal zinc monoalkylphosphate particles predominantly composed of platy crystal particles, a process for preparing the same, and cosmetics containing the same.

DETAILED DESCRIPTION OF THE INVENTION

The present invention is described in more detail below.

The alkali metal zinc monoalkylphosphates of the present invention are generally called alkali metal zinc phosphates having a saturated or unsaturated straight-chain or branched hydrocarbon group having from 8 to 32 carbon atoms. Examples of the saturated or unsaturated straight-chain or branched hydrocarbon group having from 8 to 32 carbon atoms include octyl, nonyl, decyl, dodecyl, undecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl and dotriacontyl groups. Among them, saturated straight-chain hydrocarbon groups having 12 to 18 carbon atoms are preferred from the viewpoints of performances as lubricant and as cosmetic powder with regard to the shape and size of the particles of alkyl metal zinc monoalkylphosphates. Examples of alkali metals serving as counter ions include lithium, potassium and sodium. The preferred molar ratio of atoms in the alkali metal zinc monoalkylphosphate of the present invention is zinc/alkali metal/phosphorus is 0.8–1.2/0.8–1.2/2. The preferred principal component of the alkali metal zinc monoalkylphosphate can be represented by formula (I):

(I)

wherein R represents a saturated or unsaturated straight-chain or branched hydrocarbon group having 8 to 32 carbon atoms, and A represents an alkali metal.

It is preferred that the particles of the alkali metal zinc phosphate of the present invention are predominantly composed of platy crystal particles.

The terminology "platy crystal particles" as used herein is general terminology which refers to square plate form, oblong plate form, elliptical plate form, disk form, hexagonal plate form, rhombic plate form, etc.

With regard to the size of the platy crystal particles, it is preferred that the particles meet the following requirements when observed by scanning type electron microscope:

(i) the plate length is 1 to 50 μm, (ii) the plate length/the plate thickness (plate ratio) is not lower than 2, and

(iii) the maximum plate length/the minimum plate length (plate length ratio) is not higher than 10.

The terminology "plate length" as used herein refers to a length of a side of plate in cases of square plate form, hexagonal plate form and rhombic plate form; a length of the shorter side of plate in case of oblong plate form; a length of the shorter diameter of plate in case of elliptical plate form; and a length of the diameter of plate in case of disk plate form.

The terminology "maximum plate length" as used herein refers to a length of the longer side of plate in case of oblong plate form; a length of the longest diagonal of plate in cases of hexagonal plate form and rhombic plate form; a length of the longer diameter of plate in case of elliptical plate form; and the terminology "minimum plate length" refers to a length of the shorter side of plate in case of the oblong plate form; a length of the shortest diagonal of plate in cases of hexagonal plate form and rhombic plate form; and a length of the shorter diameter of plate in case of elliptical plate form.

It is preferred that the particles of the alkali metal zinc alkylphosphate of the present invention are composed of at least 60% (in terms of the number) of the above-described platy crystal particles. When the number of the particles meeting the above-described requirements is less than 60%, there is a difficulty in obtaining cosmetics having preferred performance properties. The measurement of the number of the platy crystal particles is made by using scanning type electron microscope in the following manner. Only the number of particles having an independent shape is counted. Particles having indefinite circumference are not counted as one particle. Further, mere recesses and protrusions on the surfaces of particles or mere patterns on the surfaces thereof are not counted as one particle.

The alkali metal zinc monoalkylphosphate particles can be prepared by reacting an alkali metal salt of a monoalkylphosphoric acid represented by formula (II), said alkali metal salt having a degree of neutralization of from 0.8 to 1.2, (II)

wherein R represents a saturated or unsaturated straight-chain or branched hydrocarbon group having from 8 to 32 carbon atoms, with a zinc salt represented by formula (III)

(III)

wherein X represents zinc, Y represents an inorganic anion or an organic acid anion, and m and n each represent an integer determined by the valence requirements of Y and X, respectively, by a salt exchange, and then adjusting the pH of the reaction system to the range of from 2 to 6.

The terminology "a degree of neutralization" as used herein refers to such definitions that the degree is referred to as 0.0 when the monoalkylphosphoric acid is not neutralized, the degree is referred to as 1.0 when neutralized with an alkali metal salt to the first equivalent point, and the degree is referred to as 2.0 when neutralized with an alkali metal salt to the second equivalence point. The alkali metal salt of the monoalkylphosphoric acid (II) in the present invention generally has a degree of neutralization of from 0.8 to 1.2, and preferably from 0.9 to 1.1.

The alkali metal salt of the monoalkylphosphoric acid (II) which is used as a starting material in the present invention can be obtained by neutralizing a monoalkylphosphoric acid with an alkali metal hydroxide or by making a cation exchange thereof with a dialkali metal salt by using an ion exchange resin or an acid.

The purity of the monoalkylphosphoric acid used as a starting material in the production of the alkali metal salt of the monoalkylphosphoric acid has an effect on the crystal form of the alkali metal zinc monoalkylphosphates. The performance thereof as a lubricant is greatly affected by the purity. Hence, it is preferred that the monoalkylphosphoric acid has a purity of not lower than 80% by weight, and particularly preferably is not lower than 95% by weight.

In formula (III), Y is an inorganic anion or an organic acid anion. Examples thereof include inorganic anions such as halides, $SO_4^{2-}$, $NO_3^-$, $PO_4^{3-}$ and $OH^-$, and organic acid anions such as acetate, propionate, and citrate. Among them, inorganic anions such as halides, $SO_4^{2-}$, $PO_4^{3-}$, $NO_3^-$, and $CO_3^{2-}$ are preferred, and water-soluble Zn salts such as $ZnSO_4$ and $ZnCl_2$ are particularly preferred.

It is preferred that an alkali metal salt of a monoalkylphosphoric acid (II) is reacted with a zinc salt (III) in a reaction medium consisting of water or a mixed solvent of water and a water-soluble organic solvent, at a temperature at which the alkali metal salt of the monoalkylphosphoric acid (II) is completely dissolved. Examples of the water-soluble organic solvent include acetone, methanol, ethanol, isopropyl alcohol, n-propyl alcohol, n-butyl alcohol, sec-butyl alcohol, t-butyl alcohol, ethylene glycol, diethylene glycol, acetonitrile, tetrahydrofuran, dioxane, dimethylformamide (DMF), and dimethyl sulfoxide(DMSO). These compounds may be used either alone or as a mixture of two or more thereof. Among them, preferred are acetone, methanol, ethanol, isopropyl alcohol, and n-propyl alcohol. Water alone may be used as the solvent for the reaction. Alternatively, a mixed solvent of water and one or more water-soluble organic solvents may be used. Particularly, a mixed solvent of water and one or more members of the water-soluble solvents such as acetone, methanol, ethanol, isopropyl alcohol, and n-propyl alcohol is preferred. Water may be mixed with the water-soluble organic solvent by any of conventional methods. If desired, water-insoluble organic solvents which do not have an adverse effect may be added to the mixed solvent of water and the water-soluble organic solvent. The solvent for reaction may be formed by any of conventional methods without particular limitation.

There is no limitation with regard to the concentration of the alkali metal salt of the monoalkylphosphoric acid (II) in the solvent. However, there is a possibility that the particle size of the resulting alkali metal zinc monoalkylphosphate may be affected by the concentration. Namely, there is a tendency to reduce the average particle diameter of the resulting alkali metal zinc monoalkylphosphate with an increase in the concentration of the alkali metal salt of the monoalkylphosphoric acid (II). It is preferred from the viewpoint of performance as a lubricant that the plate diameter of the particles is from 1 to 50 μm. Hence, the concentration of the alkali metal salt of the monoalkylphosphoric acid (II) is preferably not higher than 70% by weight.

The zinc salt of the formula (III) is used in a molar ratio of at least 0.4 moles, and preferably 0.4 to 0.6 moles of zinc salt per mole of the alkali metal salt of the monoalkylphosphoric acid (II). The zinc salt (III) may be used in the form of an aqueous solution or a solid as much. When the zinc salt in the form of an aqueous solution is used, it is preferred from the viewpoint of production efficiency that the concentration of the zinc salt (III) is high.

There is no particular limitation with regard to the reaction temperature. The reaction may be carried out at a temperature at which the monoalkylphosphoric acid (II) is completely dissolved. A temperature of not lower than 70° C. is particularly preferred.

When the zinc salt (III) is added to the alkali metal salt of the monoalkylphosphoric acid (II), the pH of the reaction mixture is lower than 2 and often lower than 1.5 at 70° to 80° C. when the concentration of the monoalkylphosphoric acid is 10% by weight or higher, though the pH varies depending on the concentration of the monoalkylphosphoric acid (II) and the temperature. Hereinafter, the PH is a value measured at 70° to 80° C. The pH electrode used in the present invention is one whose guarantee temperature is 90° C. (IWAKI GLASS, pH combination electrode, CODE IWO50-BNC. LOT NO. 830027).

When the pH is lower then 2, the resulting particles of the alkali metal zinc monoalkylphosphate are a mixture of needle form and plate form, and the amount of the needle crystal is larger than that of the plate crystal in many cases. Therefore, the performance of the particles is poor as a lubricant. Namely, it is considered that the form of particles and the performance thereof as lubricant are affected by lowering in the pH of the reaction system. Hence, it is necessary to adjust the pH by using an alkaline compound.

When the pH exceeds 6 in the adjustment of the pH of the reaction system, the particles of the resulting alkali metal zinc monoalkylphosphate becomes amorphous and the performance thereof as a lubricant is greatly lowered.

Therefore, it is necessary to adjust the pH of the reaction system to from 2 to 6, and preferably from 3 to 5, to obtain the particles of the alkali metal zinc monoalkylphosphate in the form of platy crystals and to impart the desired performance as lubricants thereto. The adjustment of the pH value can be controlled by the amount of the alkaline compound to be added. The alkaline compound used for the pH adjustment is generally used in an amount of from 0.3 to 0.7 equivalents, and preferably from 0.45 to 0.55 equivalents, based on the amount of the alkali metal salt of the monoalkylphosphoric acid (II). Examples of the alkaline compound include alkali metal hydroxides. Sodium hydroxide and potassium hydroxide are particularly preferred. There is no particular limitation with regard to the adjustment of the pH value of the reaction mixture. For example, the pH adjustment may be carried out after the introduction of the zinc salt (III). Alternatively, the pH may be adjusted while the zinc salt (III) is introduced, to thereby keep the pH constant. More specifically, pH can be adjusted, for example, by a method wherein the zinc salt (III) is added to the alkali metal salt of the monoalkylphosphoric acid (II) to effect the reaction while adjusting the pH in order with the alkali metal hydroxide or a method wherein the pH is adjusted with the alkali metal hydroxide after the entire amount of the zinc salt (III) is added to the alkali metal salt of the monoalkylphosphoric acid (II).

After the termination of the reaction, the reaction mixture is cooled and the product is recovered by filtration, washed with water and dried to obtain the alkali metal zinc monoalkylphosphate particles which are predominantly composed of the above-described platy crystal particles and have excellent performance as lubricant.

The cosmetics of the present invention may contain conventional cosmetic powder in addition to the alkali metal zinc monoalkylphosphate particles as base component. Further, oil, surfactant, wetting agent, water, alcohol, antiseptic, ultraviolet ray absorber, antioxidant, perfume, etc., may be optionally blended.

Any of conventional cosmetic powders can be used. Examples thereof include inorganic extender pigments such as talc, kaolin, sericite and mica; inorganic coloring materials such as titanium oxide, zinc oxide, ultramarine, chromium oxide and iron oxide; organic coloring materials such as organic tar dyes and lake; composite pigments such as micaceous titanium and iron oxide-coated mica; and coated powders obtained by coating the surfaces of these cosmetic powders with conventional coating agents such as silicone, higher fatty acids, higher alcohols, esters and wax. These powders may be used either alone or as a mixture of two or more of them. Among these cosmetic powders, inorganic powders such as talc, kaolin, sericite, mica, titanium oxide, iron oxide, micaceous titanium and iron oxide-coated mica are particularly preferred when they are used for cosmetics, such as coszetics for makeup and cosmetics for the body.

Examples of oils used as an optional component include liquid paraffin, vaseline, paraffin wax, polyethylene wax, squalane, ceresine wax, beeswax, carnauba wax, candelilla wax, hardened castor oil, olive oil, lanolin, lanolin alcohol, lanolin fatty acid, higher alcohols, fatty acids, synthetic ester oils of higher alcohols with fatty acids and silicone. Example of the surfactant include polyoxyethylene alkyl ethers, polyoxyethylene fatty acid esters, polyoxyethylene sorbitan fatty acid esters, sorbitan fatty acid esters, glycerin fatty acid esters, polyoxyethylene hardened castor oil and polyoxyethylene sorbitol fatty acid esters. Examples of the wetting agent include sorbitol, glycerin, propylene glycol, 1,3-butylene glycol, lactic acid, sodium lactate and polyethylene glycol. Examples of the antiseptic include alkyl esters of p-hydroxytenzoic acid, sodium benzoate, potassium sorbate and phenoxyethanol. Examples of the antioxidant include tocopherol, sesamol, sesamolin and lecithin.

There is no Particular limitation with regard to the form of the cosmetics of the present invention. The cosmetics of the present invention may be in any form of powder cosmetic, oil cosmetic, emulsion cosmetic, dispersion cosmetic, etc. For example, the cosmetics of the present invention can be formulated into foundation; cosmetics for make-up such as cheek rouge, eye shadow, eye brow, and face powder; and cosmetics for the body, such as body powder and baby powder.

The alkali metal zinc monoalkylphosphate particles of the present invention are used in an amount of preferably from 0.1 to 99% (by weight; percent values below are also by weight, unless otherwise indicated) based the amount of the total composition. Particularly, in the case of pressed powder cosmetic, the amount of the particles is preferably from 0.1 to 50%. When the amount is less than the above lower limit, an effect of using said zinc salt particles can not be obtained, while when the amount is more than the above upper limit, there is a possibility that hard caking is caused on the surface of press-molded cosmetic when said surface is rubbed with a cosmetic puff many times. The cosmetic powder and optional components are used in an amount of, preferably, from 1 to 99.9% based on the amount of, the total composition. When pressed powder cosmetics are to be formulated, they are used in an amount of, preferably, from 70° to 99.9%, The amounts of the alkali metal zinc monoalkylphosphate particles, the cosmetic powder and optional components to be blended vary depending on the type of the cosmetic. However, when face powders as make-up cosmetic and foundation are to be formulated, from 10 to 50% of the alkali metal zinc monoalkylphosphate particles, from 20 to 80% of the inorganic extender pigment such as talc or sericite, from 1 to 20% of wax and oil as binders and appropriate amounts of the coloring material and perfume are blended, whereby there can be obtained cosmetics which are pleasant to the touch (such as with respect to slipperiness), adhere well to the skin and are long-lasting make-up. In the case of cosmetics for the body such as body powder, from 20 to 80% of the alkali metal zinc monoalkylphosphate particles, from 20 to 80% of the inorganic extender pigment such as talc or sericite, from 0 to 10% of oil and an appropriate amount of perf$\mu$me are blended, whereby there can be obtained cosmetics which are also pleasant to the touch.

Accordingly to the process of the present invention, there can be prepared the alkali metal zinc monoalkylphosphate particles which are mainly composed of platy crystal particles, scarcely form agglomerates and are excellent in performance characteristics such as smoothness, transparent appearance, etc., relating to use as a lubricant.

Therefore, the alkali metal zinc monoalkylphosphate particles of the present invention have excellent performance as base material for cosmetics in particular, and are suitable for use in formulating pressed face powder, powder foundation, eye shadow, etc. The particles can be used as a lubricant for another field of use by utilizing an effect of improving slipperiness in addition to cosmetics. For example, the alkali metal zinc monoalkylphosphate particle of the present invention can be used as the lubricant for mold-processing of plastic resin. More specifically, by using the particle in processing of polyvinyl chloride resin, fluidizability of the resin is improved and thereby sticking or adhesion of the resin to processing machine or processing equipment can be reduced. Therefore, undesirable elevation of temperature of the resin during the processing, which would causes residence or decomposition of the resin can be prevented, and thus, the mold-processing of the resin become easy.

The thus-obtained cosmetics of the present invention have such very excellent properties that they are very excellent in safety, smoothness, transparent appearance, adhesion and water repellency, impart wetness to the skin while spreading on the skin, are not bulky to the feel on coating and repel well water, whereas such excellent properties can not be obtained by conventional cosmetics.

The following examples and comparative examples are provided to illustrate the present invention, but are not to be construed as limiting the invention in any way.

EXAMPLE 1

50 g of monocetylphosphoric acid and 100 g of ethanol were put into a 500 ml separation flask (hereinafter referred to as "reaction vessel"). Further, a solution of 6.29 g of 96% sodium hydroxide (purity was taken into consideration by calculating it from the degree of neutralization determined by titration) dissolved in 200 g of ion-exchanged water was added thereto. After the temperature was elevated to 80° C., it was confirmed that they were clearly dissolved. The resulting solution was continuously stirred for 30 minutes. A solution of 22.3 g of zinc sulfate heptahydrate dissolved in 100 g of ion-exchanged water was added dropwise thereto to carry out a salt exchange reaction. After the completion of the dropwise addition, the mixture was stirred for 30 minutes. 8.70 g of an aqueous solution of 33.33% sodium hydroxide was then added dropwise thereto, to thereby adjust the pH of the reaction mixture to 3. Further, the mixture was stirred for one hour. After the completion of the reaction, the mixture was cooled and the product was recovered by filtration, washed with water and dried, to obtain 50.3 g of the particles of sodium zinc monocetylphosphate.

Figure 1:
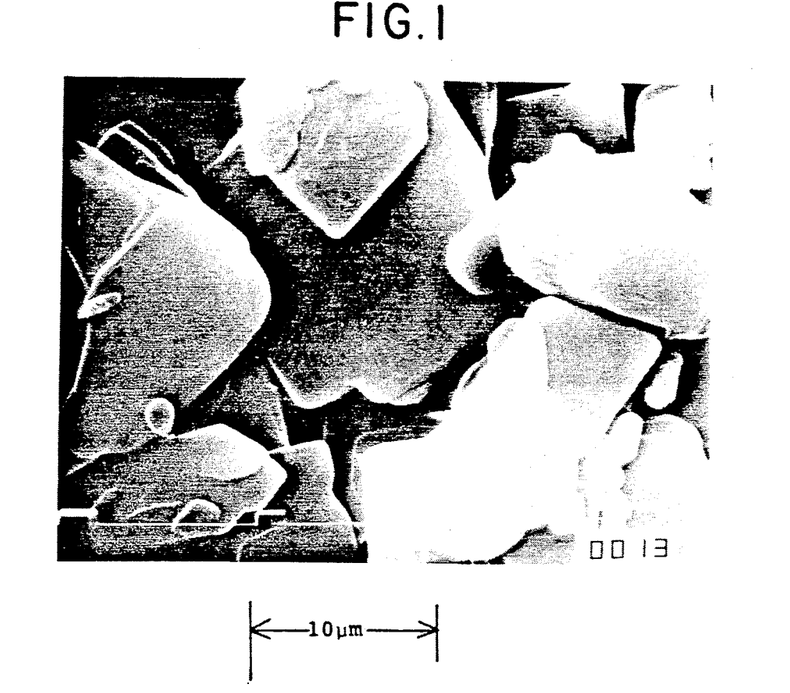
FIG. 1 is a scanning electron microscope photograph showing the crystal structure of sodium zinc monocetylphosphate obtained in Example 1.

The thus-obtained sodium zinc monocetylphosphate was inspected by a scanning electron microscope. It was found that the number of particles meeting the afore-mentioned requirements (i) to (iii) accounts for 95% of the entire particles. FIG. 1 is a scanning electron micrograph (scale: 10 μm).

The particles were subjected to elemental analysis and it was found that the particle was sodium zinc monocetylphosphate having the empirical formula $C_{32}H_{67}NaO_8P_2Zn$. The results of the elemental analysis are indicated below.

|  | Elemental analysis: | | | | |
| --- | --- | --- | --- | --- | --- |
|  | C | H | Na | P | Zn |
| Calculated (%) | 52.6 | 9.2 | 3.2 | 8.5 | 9.0 |
| Found (%) | 53.3 | 9.7 | 3.0 | 8.9 | 9.1 |

Infrared absorption spectrum of the particle is shown

Figure 3:
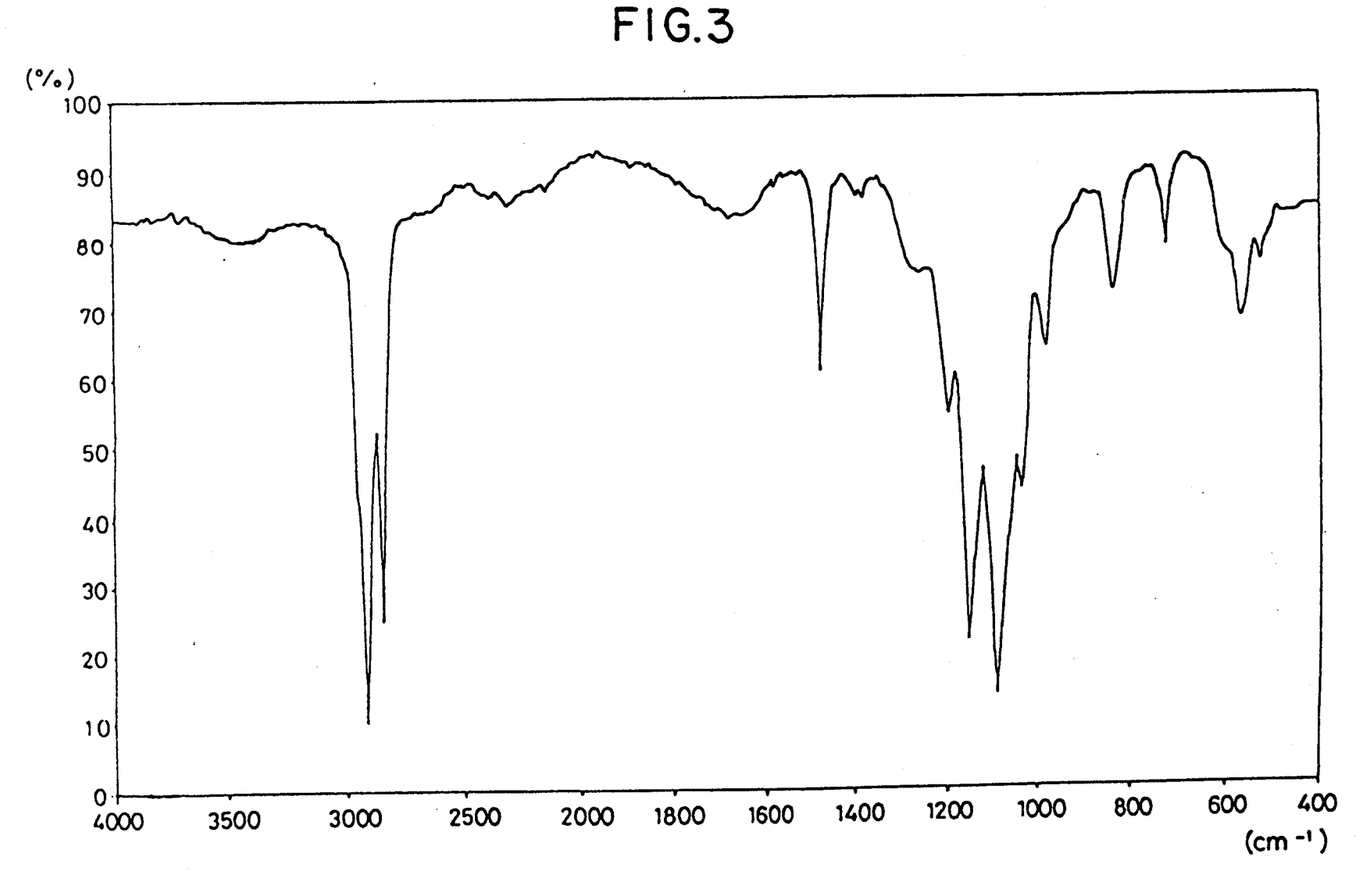
FIG. 3 is infrared absorption spectrum of sodium zinc monocetylphosphate obtained in Example 1.

| Measuring device: | Model 270-30 manufactured by Hitachi, Ltd. |
| --- | --- |
| Measuring method: | Pelleted with potassium bromide |
| 2920 cm$^{-1}$, 2848 cm$^{-1}$ | C—H stretching vibration |
| 1470 cm$^{-1}$ | C—H deformation vibration |
| 1197 cm$^{-1}$, 1152 cm$^{-1}$ | P=O and C—O—P stretching vibration |
| 1089 cm$^{-1}$, 1032 cm$^{-1}$ | |

EXAMPLE 2

50 g of monocetylphosphoric acid and 100 g of ethanol were placed in a 500 ml reaction vessel. Further, a solution of 6.29% of 96% sodium hydroxide (purity was taken into consideration by calculating it from the degree of neutralization determined by titration) dissolved in 200 g of ion-exchanged water was added thereto. After the temperature was elevated to 80° C., it was confirmed that they were clearly dissolved. The solution was continuously stirred for 30 minutes. A solution of 22.3 g of zinc sulfate heptahydrate dissolved in 100 g of ion-exchanged water was added dropwise thereto to carry out a salt exchange reaction. After the completion of the dropwise addition, the mixture was stirred for 30 minutes. 9.30 g of an aqueous solution of 33.33% sodium hydroxide was added dropwise thereto, to thereby adjust the pH of the reaction mixture to 5. Further, the mixture was stirred for one hour. After the completion of the reaction, the reaction mixture was cooled and the product was recovered by filtration, washed with water and dried, to obtain 51.2 g of the particles of sodium zinc monocetylphosphate.

The thus-obtained sodium zinc monocetylphosphate was examined by a scanning electron microscope and it was found that the number of particles meeting the afore-mentioned requirements (i) to (iii) accounted for 93% of the total number of particles.

EXAMPLE 3

50 g of monooctylphosphoric acid and 100 g of ethanol were placed in a 500 ml reaction vessel. Further, a solution of 9.52 g of 96% sodium hydroxide (purity was taken into consideration by calculating it from the degree of neutralization determined by titration) dissolved in 200 g of ion-exchanged water was added thereto. After the temperature was elevated to 80° C., it was confirmed that they were dissolved. The solution was continuously stirred for 30 minutes. A solution of 34.2 g of zinc sulfate heptahydrate dissolved in 100 g of ion-exchanged water was added dropwise thereto. After the completion of the addition, the mixture was stirred for 30 minutes. 14.26 g of an aqueous solution of 33.33% sodium hydroxide was added dropwise thereto, to thereby adjust the pH of the reaction mixture to 5. Further, the mixture was stirred for one hour. After the completion of the reaction, the reaction mixture was cooled, and the product was collected by filtration, washed with water and dried to obtain 49.6 g of the particles of sodium zinc monooctylphosphate.

The thus-obtained sodium zinc monooctylphosphate was inspected by a scanning electron microscope and it was found that the ratio of particles meeting the afore-mentioned requirements (i) to (iii) was 95% (in terms of the number) of the total number of particles.

EXAMPLE 4

50 g of monolaurylphosphoric acid and 100 g of ethanol were put into a 500 ml reaction vessel. Further, a solution of 7.83 g of 96% sodium hydroxide (purity was taken into consideration by calculating it from the degree of neutralization determined by titration). dissolved in 200 g of ion-exchanged water was added thereto. After the temperature was elevated to 80° C., it was confirmed that they were dissolved. Further, the solution was continuously stirred for 30 minutes. A solution of 28.1 g of zinc sulfate heptahydrate dissolved in 100 g of ion-exchanged water was added dropwise thereto to carry out a salt exchange reaction. After the completion of the addition, the mixture was stirred for 30 minutes. 11.75 g of an aqueous solution of 33.33% sodium hydroxide was added dropwise thereto to adjust the pH of the reaction mixture to 5. Further, the mixture was stirred for one hour. After the completion of the reaction, the reaction mixture was cooled and the product was recovered, washed with water and dried, to obtain 49.6 g of the particles of sodium zinc monolaurylphosphate.

The thus-obtained sodium zinc monolaurylphosphate was inspected by a scanning electron microscope and it was found that the number of particles meeting the afore-mentioned requirements (i) to (iii) accounted for 92% of the total number of particles.

EXAMPLE 5

50 g of monostearylphosphoric acid and 100 g of ethanol were put into a 500 ml reaction vessel. Further, a solution of 5.94 g of 96% sodium hydroxide (purity was taken into consideration by calculating it from the degree of neutralization determined by titration) dissolved in 200 g of ion-exchanged water was added thereto. After the temperature was elevated to 80° C., it was confirmed that they were clearly dissolved. The solution was continuously stirred for 30 minutes. A solution of 21.4 g of zinc sulfate heptahydrate dissolved in 100 g of ion-exchanged water was added dropwise thereto to carry out a salt exchange reaction. After the completion of the addition, the mixture was stirred for 30 minutes. 8.85 g of an aqueous solution of 33.33% sodium hydroxide was added dropwise thereto to adjust the pH of the reaction mixture to 3. Further, the mixture was stirred for one hour. After the completion of the reaction, the mixture was cooled and the product was collected by filtration, washed with water and dried, to obtain 51.5 g of the particles of sodium zinc monostearylphosphate.

The thus-obtained sodium zinc monostearylphosphate was inspected by a scanning electron microscope and it was found that the number of particles meeting the afore-mentioned requirements (i) to (iii) accounted for 93% of the total number of particles.

COMPARATIVE EXAMPLE 1

50 g of monocetylphosphoric acid and 100 g of ethanol were put into a 500 ml reaction vessel. Further, a solution of 6.29 g of 96% sodium hydroxide (purity was taken into consideration by calculating it from the degree of neutralization determined by titration) dissolved in 200 g of ion-exchanged water was added thereto. After the temperature was elevated to 80° C., it was confirmed that they were clearly dissolved. The solution was continuously stirred for 30 minutes. A solution of 22.3 g of zinc sulfate heptahydrate dissolved in 100 g of ion-exchanged water was added dropwise thereto to carry out a salt exchange reaction. After the completion of the addition, the mixture was stirred for 2 hours. The pH of the reaction mixture was 1.35 at the end of the reaction. The mixture was cooled and the product was collected by filtration, washed with water and dried, to obtain 51.4 g of the particles of zinc monocetylphosphate (zinc/sodium/phosphorus=0.88/0.49/2.00).

Figure 2:
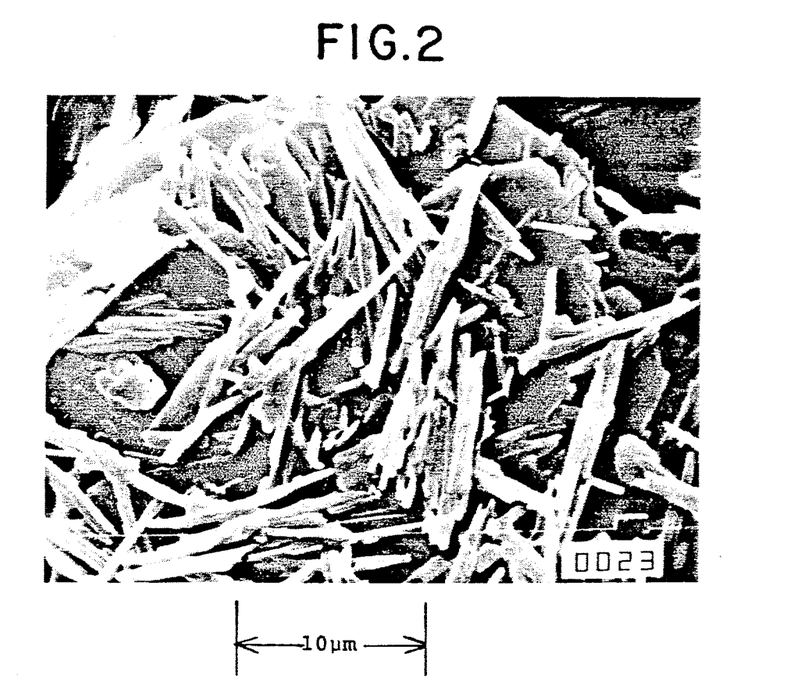
FIG. 2 is a scanning electron microscope photograph showing the crystal structure of zinc monocetylphosphate obtained in Comparative Example 1.

The thus-obtained zinc monocetylphosphate was inspected by a scanning electron microscope, and it was confirmed that the product was a mixture of needle crystal and platy crystals The scanning electron micrograph is shown in FIG. 2 (scale: 10 μm).

COMPARATIVE EXAMPLE 2

50 g of monocetylphosphoric acid and 100 g of ethanol were put into a 500 ml reaction vessel. Further, a solution of 6.29 g of 96% sodium hydroxide (purity was taken into consideration by calculating it from the degree of neutralization determined by titration) dissolved in 200 g of ion-exchanged water was added thereto. After the temperature was elevated to 80° C., it was confirmed that they were clearly dissolved. The solution was continuously stirred for 30 minutes. A solution of 22.3 g of zinc sulfate heptahydrate dissolved in 100 g of ion-exchanged water was added dropwise thereto to carry out a salt exchange reaction. After the completion of the addition, the mixture was stirred for 30 minutes. 13.20 g of an aqueous solution of 33.33% sodium hydroxide was added dropwise thereto to adjust the pH of the reaction mixture to 6.6. Further, the mixture was continuously stirred for one hour. After the completion of the reaction, the mixture was cooled and the product was collected by filtration, washed with water and dried, to obtain 49.3 g of the particles of zinc monocetylphosphate (zinc/sodium/phosphorus=0.77/1.42/2.00).

The thus-obtained zinc monocetylphosphate was inspected by a scanning electron microscope, and it was found that the shape of the powder was indefinite, i.e., the product was neither platy crystal nor needle crystal, and the product was an amorphous aggregate.

EXAMPLE 6

Sodium zinc cetylphosphate particles obtained in Example 1 were subjected to organoleptic evaluation on the touch. Zinc cetylphosphates obtained in Comparative Examples 1 and 2, zinc stearate, talc, mica and nylon powder were used as comparative products.

The results are shown in Table 1.

EVALUATION METHOD

Evaluation on the touch of the powders themselves was made by expert panel. Mica was used as standard material. Evaluation of mica was referred to as 3. Grading criterion were as follows;

5: Good in comparison with standard material
4: Slightly good in comparison with standard material
3: Equal to standard material
2: Slightly poor in comparison with standard material
1: Poor in comparison with standard material

TABLE 1

|  | Sample | Smoothness | Adhesion | Adaptability | Transparent appearance | Water repellency | Overall evaluation |
|---|---|---|---|---|---|---|---|
| Product of invention | Sodium zinc monocetylphosphate of Ex. 1 | 5 | 5 | 5 | 5 | 5 | 5 |
|  | Sodium zinc monocetylphosphate of Ex. 2 | 5 | 5 | 5 | 5 | 5 | 5 |
| Comparative product | Zinc monocetylphosphate of Comp. Ex. 1 | 4.5 | 5 | 4 | 2 | 5 | 4 |
|  | Zinc monocetylphosphate of Comp. Ex. 2 | 1 | 2 | 1 | 3 | 5 | 2 |
|  | Mica | 3 | 3 | 3 | 3 | 3 | 3 |
|  | Talc | 2.5 | 3 | 4 | 2 | 3 | 3 |
|  | Zinc stearate | 1 | 4 | 4 | 1 | 4 | 2 |
|  | Nylon powder | 4 | 1 | 1 | 3 | 2 | 2 |

EXAMPLE 7

Pressed Face Powder

A pressed face powder having the following formulation was prepared by using sodium zinc monocetylphosphate particles obtained in Example 1 in the following manner. Evaluation was made in comparison with comparative products. Zinc monocetyl phosphate obtained in Comparative Example 2 and products using talc and mica were used as comparative products.

| Blended component | Formulation Amount (%) | | |
|---|---|---|---|
| | Product of invention | Comparative product 1 | Comparative product 2 |
| Sodium zinc monocetylphosphate of Ex. 1 | 30 | — | — |
| Zinc monocetylphosphate of Comp. Ex. 2 | — | 30 | — |
| Talc | balance | balance | balance |
| Mica | 40 | 40 | 40 |
| Red iron oxide | 0.1 | 0.1 | 0.1 |
| Liquid paraffin | 4 | 4 | 4 |
| Perfume | 0.1 | 0.1 | 0.1 |
| Total | 100 | 100 | 100 |

PREPARATION METHOD

The powder components were mixed, crushed and fed to a Henshel mixer. Oil and perfume were added thereto, and the mixture was mixed to make it homogeneous. The mixture was press-molded into a container, thus obtaining a product.

The thus-obtained face powders were evaluated by an expert panel.

The results are shown in Table 2.

TABLE 2

| Sample | Smoothness | Adhesion | Adaptability | Transparent appearance | Overall evaluation |
|---|---|---|---|---|---|
| Product of invention | 5 | 5 | 5 | 5 | 5 |
| Comparative product 1 | 4 | 5 | 4 | 3 | 4 |
| Comparative product 2 | 3 | 3 | 3 | 3 | 3 |

Comparative product 2 was used as a standard and designated as having value of 3. Grading criterion were according to Example 6.

It is seen that the cosmetic of the present invention is face powder which is superior to comparative products in spreadability as well as adaptability and transparent appearance.

EXAMPLE 8

Powder Foundation

| Formulation | (%) |
|---|---|
| Sodium zinc monocetylphosphate of Example 1 | 20 |
| talc | balance |
| sericite | 10 |
| Titanium oxide | 1 |
| Red iron oxide | 1.5 |
| Black iron oxide | 0.2 |
| Yellow iron oxide | 2.0 |
| Finely divided wax (PRESS-AID, manufactured by PRESPERSE Inc.) | 10 |
| Perfume | 0.1 |
| Total | 100 |

PREPARATION METHOD

The powder components were mixed, crushed, and fed to Henshel mixer. Perfume was added thereto and the mixture was mixed to make it homogeneous. The mixture was press-molded into a container to obtain a product. The thus-obtained foundation was excellent in touch-related properties, such as spreadability, etc., and had excellent adaptability to the skin.

EXAMPLE 9

Loose Type Face Powder

| Formulation | (%) |
|---|---|
| Sodium zinc monocetylphosphate of Example 1 | 50 |
| talc | balance |
| Red iron oxide | 0.1 |
| Liquid paraffin | 1 |
| Perfume | 0.1 |
| Total | 100 |

PREPARATION METHOD

The powder components were mixed, crushed and fed to a Henshel mixer. Oil and perfume were added thereto and the mixture was mixed to make it homogeneous. The resulting mixture was sieved to obtain a product.

The thus-obtained loose type face powder was well-spreadable and superior to a conventional loose type face powder that was powdery.

EXAMPLE 10

Oil Type Face Powder

| Formulation | (%) |
|---|---|
| Sodium zinc monocetylphosphate of Example 1 | 20 |
| Talc | balance |
| Kaolin | 5 |
| Titanium oxide | 5 |
| Red iron oxide | 1.0 |
| Black iron oxide | 0.1 |
| Yellow iron oxide | 0.6 |
| Squalene | 25 |
| Isopropyl palmitate | 15 |
| Ceresine | 7 |
| Perfume | 0.1 |
| Total | 100 |

PREPARATION METHOD

The powder components were mixed and crushed. Separately, the oil component was dissolved by heating and added thereto with stirring. The mixture was mixed to make it homogeneous. The mixture was charged into a container and cooled to obtain a product.

EXAMPLE 11

Creamy Foundation

| | Formulation | (%) |
|---|---|---|
| 1. | Stearic acid | 5 |
| 2. | Lipophilic glycerin monostearate | 2.5 |
| 3. | Cetostearyl alcohol | 1 |
| 4. | Propylene glycol monolaurate | 3 |
| 5. | Squalene | 7 |
| 6. | Olive oil | 8 |
| 7. | Purified water | balance |
| 8. | Antiseptic | 0.1 |
| 9. | Triethanolamine | 1.2 |
| 10. | Sorbitol | 3 |
| 11. | Titanium oxide | 5 |
| 12. | Sodium zinc monocetylphosphate of Example 1 | 15 |
| 13. | Red iron oxide | 1.0 |
| 14. | Black iron oxide | 0.1 |
| 15. | Yellow iron oxide | 0.6 |
| 16. | Perfume | 0.1 |
| | Total | 100 |

PREPARATION METHOD

The powder components (11 to 15) were mixed and crushed. Separately, the water phase components (7 to 10) were mixed to prepare a solution. The crushed pigments were dispersed therein and the dispersion was heated to 75° C. The oil components (1 to 6) were dissolved by heating and added to the previously prepared water phase with stirring to emulsify them. The emulsion was cooled with stirring and perfume was added thereto at 50° C. The mixture was cooled with stirring.

While the present invention has been described in detail and with reference to specific embodiments thereof, it is apparent to one skilled in the art that various changes and modifications can be made therein without departing from the spirit and the scope of the present invention.

What is claimed is:

1. A cosmetic containing particles of an alkali metal zinc monoalkylphosphate represented by formula (I):

wherein R represents a saturated or unsatured straight-chain or branched hydrocarbon group having from 8 to 32 carbon atoms, and A represents an alkali metal.

2. A cosmetic as claimed in claim 1, wherein the molar ratio of zinc/alkali metal/phosphorus is 0.8–1.2/0.8–1.2/2 by molar ratio.

3. A cosmetic as claimed in claim 1, wherein said alkali metal zinc monoalkylphosphate is in the form of particles mainly composed of platy crystal particles.

4. A cosmetic as claimed in claim 3, wherein said platy crystal particles meet the following requirements when inspected by a scanning electron microscope:
   (i) the plate length is 1 to 50 μm,
   (ii) the plate length/plate thickness (plate ratio) is not lower than 2, and
   (iii) the maximum plate length/the minimum plate length (plate length ratio) is not higher than 10,
   and the number of said platy crystal particles accounts for at least 60% of the total number of particles of the alkali metal zinc monoalkylphosphate.

* * * * *